United States Patent [19]

Izrael

[11] 4,371,521

[45] Feb. 1, 1983

[54] PHARMACEUTICAL COMPOSITION FOR RETARDING EXCESSIVE PLATELET AGGREGATION

[76] Inventor: Victor Izrael, 22 rue des Francs Bourgeois, Paris, France

[21] Appl. No.: 478,367

[22] Filed: Jun. 11, 1974

[30] Foreign Application Priority Data

Jun. 27, 1973 [FR] France ................. 73 23441

[51] Int. Cl.³ ............... A61K 31/66; A61K 37/48
[52] U.S. Cl. .................................. 424/94; 424/212
[58] Field of Search ................... 424/94, 211, 212

[56] References Cited

U.S. PATENT DOCUMENTS 3,539,625  11/1970  Nordmann et al. ................. 260/534

OTHER PUBLICATIONS

Chemical Abstracts 68:112705u (1968).
Gaarder et al., 192 Nature (Lond.) 531–532 (1961).
Born, 194 Nature (Lond.) 927–928 (1962).
Nordöy et al., 1 Scand. J. Hemat., 16–25 (1964).
Rozenberg et al.–Biochemica et Biophysica ACTA, pp. 280–288 (1968).
The Enzymes, Ed. Boyer et al. vol. 6 (1962), chapter 31, pp. 516–520.
Platelets: Product, Function, Transfusion & Storage; Izrael et al., pp. 187–196 (1974).

*Primary Examiner*—Leonard Schenkman
*Attorney, Agent, or Firm*—Wegner & Bretschneider

[57] ABSTRACT

The invention provides a method of treating thromboembolic conditions, stress and/or visceral cellular insufficiency in mammals, the method comprising administering to the mammal effective amounts of creatine-phosphate and creatine-phosphokinase. The invention also provides a pharmaceutical composition suitable for use in the method.

3 Claims, No Drawings

PHARMACEUTICAL COMPOSITION FOR RETARDING EXCESSIVE PLATELET AGGREGATION

The present invention relates to a pharmaceutical composition having useful pharmacological properties and to a method of treating thrombo-embolic conditions, stress and/or visceral cellular insufficiency in mammals.

The composition comprises creatine-phosphokinase (CPK) and creatine phosphate (CP) and a pharmaceutically acceptable solvent.

Neither the substrate (CP) alone (i.e. in the absence of the administration of the enzyme which brings about its conversion) nor the enzyme (CPK) alone gives the pharmacological results discussed below.

The two compounds CPK and CP, as well as the products resulting from the enzyme reaction, are substances which occur naturally in the human organism.

Their therapeutic effect depends on their direct introduction into the blood and the extracellular medium; in nature, they are present only in the intra-cellular medium of some cells, and always in the cells of striated muscle.

The principle of the therapeutic use is based on the following biochemical reaction (the Lohmann reaction)

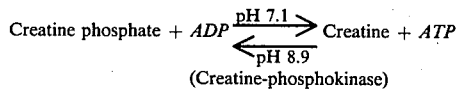
(Creatine-phosphokinase)

In the presence of the enzyme CPK, the substrate CP can yield the energy from its energy-rich bond to the adenosine-diphosphate (ADP) of the medium, the free energy of the hydrolysis of CP being less than that of ADP. At the pH of the blood, namely 7.40, the direction of the reaction is from the left to the right, and ADP is converted to adenosine-triphosphate (ATP).

The pharmacological effects of the CPK/CP combination thus result from a double biochemical effect:

(1) a "clearing" of the plasma ADP; this molecule plays a major role in physiological platelet aggregation, conditions of excessive tendency towards platelet aggregation and thrombosis mechanisms; and (2) an accumulation of ATP; this molecule is a major energy fuel necessary for numerous cellular biochemical reactions, and plays a part especially in cellular synthesis and anabolism reactions.

The creatine formed during the reaction is an atoxic and non-reactive physiological substance which exists naturally in the blood in an amount of 30 to 40 mg/liter and is very rapidly eliminated by the kidneys.

A portion of this creatine is converted in vivo into creatinine, a substance which is also atoxic and non-reactive, and exists physiologically in the blood in an amount of 8 to 12 mg/liter, and is also very rapidly eliminated by the kidneys (renal clearance of creatinine = 120 ml/minute).

In the pharmaceutical compositions according to the invention the weight ratio of creatine-phosphokinase to creatine-phosphate is preferably 1:30 to 3000, especially substantially 1:400.

The pharmaceutical compositions can be made in the form of lyophilised powder to be dissolved at the time of use. The invention therefore also provides a solid composition suitable for preparing the pharmaceutical compositions of the invention and comprising creatine-phosphate and creatine-phosphokinase.

The solvent can be distilled water or saline serum, for example physiological serum containing 9 g/liter of sodium chloride. The concentration of the pharmaceutical composition with respect to CP in the solution ready for injection can be, for example, 1 g/10 ml of solvent and that of CPK can be 2.5 mg/10 ml of solvent.

Furthermore, it is possible to administer the two substances creatine-phosphate and creatine-phosphokinase successively in either order whatsoever, each dissolved either in distilled water or in a physiological solution in the same ratios by weight as those given above for the simultaneous administration.

Creatine-phosphate is a substance which is widely found in vertebrates; it is present especially in striated muscle, in a proportion of 3 to 6 g/kg of fresh muscle. It is a guanidine derivative having the formula:

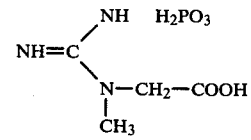

Its activity is derived from the presence of the amidine-phosphate group, which contains an energy-rich bond (bond energy ~ 10 kcal/mole). It can be easily synthesised by various methods, especially that of Ennor and Stocken, Biochemical Preparations, Volume 5, pages 9–12, John Wiley and Sons, New York, 1957. The product can be obtained in pure and crystalline form.

Creatine-phosphokinase is an enzyme which is also widely found in vertebrates; it is found especially in striated and cardiac muscle and cerebral tissue. It is a protein molecule of molecular weight $8.1 \times 10^4$. Its aminoacid composition and physical and chemical properties are the subject of a complete review by Kuby and Noltmann [The Enzymes, edited by Boyer, Lardy and Myrbäck, Academic Press, N.Y. and London—2nd edition, 1962]. The enzyme can be obtained in crystalline form from rabbit skeletal muscle.

Various methods for isolating it are known; it is possible to recover, after crystallisation, 60 to 80% of the enzyme activity of the original extract. Examples of these methods are: Kuby, Noda and Lardy, J. Biol. Chem., 1954, 209, 191; Mahowald, Noltmann and Kuby, ibid, 1962, 237, 1535; Noda, Nihei and Morales, ibid, 1960, 235, 2830.

Compositions containing creatine-phosphokinase and creatine-phosphate in physiological solution were tested in the following pharmacological experiments given in the Example below. In the Example, CP = creatine-phosphate, f = final, and CPK = creatine-phosphokinase.

Creatine-phosphate alone and creatine phosphokinase alone were administered in the form of physiological solutions. The expression "CP/CPK combination" means a pharmaceutical composition containing creatine-phosphate and creatine phosphokinase in physiological serum.

EXAMPLE

1. Toxicity (1) Acute toxicity

The determination, in male albino mice, of the $LD_{50}$ and of the standard deviation (calculated according to Tainter and Miller, Proc. Soc. Exptl. Biol. Med., 1944, 57, 261–264) showed a rather low acute toxicity:

| | |
|---|---|
| CP alone | $LD_{50} = 3.5 \pm 0.12$ g/kg |
| CPK alone | $LD_{50} > 0.1$ g/kg |
| CP + CPK (at the rate of one part of CPK per 400 parts of CP) | $LD_{50} - 4.2 \pm 0.07$ g/kg |

(2) Chronic toxicity

A daily dose of CP (0.05 g/kg) and CPK (1 mg/kg) dissolved in physiological solution was administered over 2 months to Wistar rats weighing 200 g, and over 3 months to Bouscat rabbits weighing 2.5 kg. Growth disorders, or changes in the haemogram or histological deterioration of the heart, liver, kidneys, spleen and suprarenal glands were not observed.

2. Pharmacological Properties (1) Pharmacological properties *in vitro*

Investigations using human blood, human plasma rich in platelets (PRP) and human plasma with a low platelet count (PLPC) were made.

A - Pharmacokinetic investigation:

(a) The kinetics of the enzyme reaction in various buffers and at various pHs are known: the Michaelis constant for ADP is $8 \times 10^{-4}$ to $1 \times 10^{-3}$ mol/liter, and for creatine-phosphate it is $5 \times 10^{-3}$ mole/liter; the $R_{max}$ for ADP is 1.7 μmols/minute/μg of protein, and for creatine-phosphate is 1.1 μmols/minute/μg of protein (see Kuby, Noda and Lardy, J. Biol. Chem., 1954, 210, 65; Askonas Thesis, University of Cambridge, 1952).

The presence of calcium and magnesium ions is necessary for the reaction; these two cations do in fact exist in plasma at the favourable concentrations of, respectively, 5 mEq/1 and 2 mEq/1.

(b) In human plasma, at 37° and at pH 7.40, the enzyme kinetics were investigated by making measurements of the ADP consumed and of the ATP formed, using the luciferin-luciferase method of determination.

In this way, it was established that, when ADP at a concentration of $2.5 \times 10^{-5}$ M f. was introduced into human plasma containing creatine-phosphate (50 μM/ml f.) and creatine-phosphokinase (40 μg/ml f.), more than 50% of the ADP added was consumed in less than 5 seconds, and more than 80% of the ADP was converted to ATP in less than 10 seconds; the kinetics of the reaction are according to the Michaelis concept, and equilibrium is reached in 15 seconds.

Under the same conditions of CP and CPK concentration, the CP/CPK enzyme activity persists in the plasma for more than 72 hours at 4°, more than 48 hours at 22° and more than 24 hours at 37°.

B - Effect of the CP/CPK combination on platelet aggregation.

ADP plays a fundamental role in platelet aggregation, or the first stage of haemostasis, no matter what the agent which induces aggregation may be (Mustard and Packham, Pharmacol. Review. 1970, 22, 97–187). Intrinsic ADP, liberated by the platelets into the plasma during the "release" phase, is involved.

By means of investigations using a Born aggregation meter and checks using a phase contrast microscope, it has been shown that the CP/CPK combination, by clearing the plasma of ADP, was a powerful inhibitor of platelet aggregation, no matter what the agent inducing aggregation may be.

(a) After incubating human PRP (Plasma rich in platelets) for one minute at 37° in the presence of CP/CPK (at respective concentrations of 50 μM/ml f. and 40 μg/ml f.), the aggregation of platelets under the effect of ADP ($5 \times 10^{-7}$ to $5 \times 10^{-6}$ Mf.) or collagen (20 μg/ml f.) or thrombin (0.05 to 0.075 μ/ml f.) or adrenalin (2 μg/ml f.) is completely suppressed.

(b) Furthermore, if the CP/CPK combination is added to PRP in a second phase, i.e. the platelets have already aggregated (under the effect of ADP, thrombin or adrenalin), rapid disaggregation takes place and the separated platelets become completely re-suspended. The platelets thus disaggregated retain their normal function, and are in particular capable of re-aggregating under the effect of a new stimulus of ADP.

C - Effect on blood cells.

It has been verified that, both *in vitro* and *in vivo*, the CP/CPK combination, even at high concentrations, does not have any harmful effect on blood cells: in particular, in the presence of the CP/CPK combination, the proportion of nucleotides in the red corpuscles and the platelets, the power of the platelets to incorporate serotonin marked with $^{14}C$ and the phagocytic power of the polynuclear cells were not altered.

Furthermore, the presence of the CP/CPK combination permits better storage of blood cells *in vitro*: thus, in the presence of the CP/CPK combination, after storing PRP for 3 days at 4° whilst rotating it slowly, the number of platelets recovered is 100% and the platelets are still functioning; after storing polynuclear cells for 8 days at 4° whilst rotating them slowly, the phagocytic and bactericidal power of the polynuclear cells is still retained.

Thus the CP/CPK system finds an additional therapeutic application in blood banks, as an additive which, when introduced into suspensions of blood cells for transfusion into patients, permits prolonged storage and better preservation of these cells.

(2) Pharmacological properties *in vivo*

A. Effect on haemostasis

The inhibiting effect of the CP/CPK combination on platelet aggregation and primary haemostasis manifests itself *in vivo* by an anti-thrombotic and anti-coagulant effect which was checked on animals by means of the following experiments:

(a) After a single intravenous injection of CP/CPK at respective doses of 125 mg/kg and 0.31 mg/kg, into rats, the bleeding time is prolonged by 30%;

(b) The CP/CPK combination prevents or reduces experimental thromboses induced in rats by ADP; and (c) A continuous intravenous perfusion of the CP/CPK combination, dissolved in physiological serum, prevents, in rabbits, "disseminated intravascular coagulation" which normally accompanies the generalised Schwartzman phenomenon, as induced by two successive injections at a 24 hour interval of *Colibacillus* endotoxin at a dose of 50 μg/kg of body weight.

B. Effect on cellular metabolism

The cellular provision of energy from energy-rich bonds and especially ATP, permits better cellular metabolism and better cellular defence during many conditions of stress or visceral insufficiency. For example:

(a) the cardiac contraction of hearts isolated from frogs is markedly increased in the presence of the CP/CPK combination; and (b) the period of survival after complete hepatectomy is doubled in rabbits which are subjected to a continuous perfusion of the CP/CPK combination.

The pharmacological experiments show that the pharmaceutical compositions containing creatine-phosphokinase and creatine-phosphate in physiological solution possess valuable pharmacological properties.

The therapeutic applications of the invention are as follows:

(1) Prevention and treatment of thrombo-embolic conditions such as phlebitis, arterial embolisms, arteritis obliterans, angina, myocardial infarction, post-surgical thrombo-embolic complications, disseminated intravascular coagulation and Moschowictz's disease.

The major advantage of the invention over conventional anti-coagulant treatments (using heparin and anti-vitamins K) is that the CP/CPK combination acts on primary haemostasis and thus at the initial stage of the build-up of thrombosis and not at the already too late stage of plasma coagulation, and it does not involve serious haemorrhegic risks due to overdoses.

(2) Treatment of conditions of stress and visceral cellular insufficiency such as shock, comas and septicaemias, hepatic cellular insufficiency, serious hepatitis, cirrhosis, cardiac insufficiency, some nephropathies, cerebral ischemia, medullar insufficiencies, haemolytic anaemias and various haemopathies.

The CP/CPK combination can be administered parenterally, e.g. by intramuscular administration, by direct intravenous administration, or by intravenous perfusion.

The dose can be 0.5 to 3 g/day of creatine-phosphate and 1 mg to 100 mg/day of creatine-phosphokinase.

The two substances in question can be packaged in the same bottle or in separate bottles, in lyophilised form, mixing in the second case being effected at the time of use if the two substances are to be injected simultaneously.

It is also possible to inject creatine-phosphate and creatine-phosphokinase dissolved in physiological solution, one after the other with a short interval between.

I claim:

1. A liquid solution capable of being directly injected into the bloodstream in dosage unit form which comprises creatine-phosphate and creatine-phosphokinase and a pharmaceutically acceptable solvent, there being present in said liquid solution from 30 to 3000 parts by weight of creatine-phosphate per single part by weight of creatine-phosphokinase.

2. A method of retarding excessive platelet aggregation in a patient which comprises administering directly to the bloodstream creatine-phosphokinase and creatine-phosphate in a weight ratio of creatine-phosphokinase:creatine-phosphate of from 1:30 to 1:3000.

3. A method of claim 2 wherein said weight ratio is about 1:400.

* * * * *

UNITED STATES PATENT AND TRADEMARK OFFICE
CERTIFICATE OF CORRECTION

PATENT NO. : 4,371,521
DATED : February 1, 1983
INVENTOR(S) : Victor Izrael

It is certified that error appears in the above-identified patent and that said Letters Patent is hereby corrected as shown below:

On the cover sheet of the patent please insert:

--Assignee: Laboratoires Biotherax, France--

Signed and Sealed this

Eleventh Day of September 1984

[SEAL]

Attest:

GERALD J. MOSSINGHOFF

Attesting Officer    Commissioner of Patents and Trademarks